United States Patent [19]

Kleemann et al.

[11] 4,374,995
[45] Feb. 22, 1983

[54] PROCESS FOR THE PRODUCTION OF TRYPTOPHANE-HYDANTOIN

[75] Inventors: Axel Kleemann; Marc Samson, both of Hanau, Fed. Rep. of Germany

[73] Assignee: Degussa Aktiengesellschaft, Frankfurt, Fed. Rep. of Germany

[21] Appl. No.: 320,128

[22] Filed: Nov. 10, 1981

[30] Foreign Application Priority Data

Nov. 15, 1980 [DE] Fed. Rep. of Germany ....... 3043259

[51] Int. Cl.³ .......................................... C07D 233/30
[52] U.S. Cl. .................................................. 548/309
[58] Field of Search ....................... 548/309; 564/251

[56] References Cited

U.S. PATENT DOCUMENTS 2,725,384 11/1955 Burness ............................. 564/251
3,419,551 12/1968 Suzuki et al. ....................... 548/309

FOREIGN PATENT DOCUMENTS 715578 8/1965 Canada ................................ 548/309

55-136279 10/1980 Japan ................................... 548/309

Primary Examiner—Ethel G. Love
Attorney, Agent, or Firm—Cushman, Darby & Cushman

[57] ABSTRACT

Tryptophane hydantoin is prepared by
(a) reacting a compound of the general formula

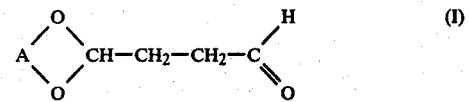

where A is an alkylene group having 2 or 3 carbon atoms or such an alkylene group substituted by 1 to 2 methyl groups in aqueous or aqueous alcoholic solution with hydrogen cyanide or a cyanide ion supplying compound, ammonia or an ammonium ion supplying compound and carbon dioxide or a carbonate ion supplying compound and
(b) reacting the reaction mixture obtained with phenyl hydrazine at a pH between 0.1 and 4.

10 Claims, No Drawings

PROCESS FOR THE PRODUCTION OF TRYPTOPHANE-HYDANTOIN

BACKGROUND OF THE INVENTION

Tryptophane is an essential aminoacid which frequently represents the limiting aminoacid in fodders and mixed fodders. Since tryptophane can be obtained by alkaline hydrolysis of tryptophanehydantoin, this synthesis has great significance.

There are already known an entire series of processes for the production of tyrptophanehydantoin, which ultimately start from either acrolein or acrylonitrile and proceed via several steps. The known processes, however, throughout are not completely satisfactory because they either require the use of difficult accessible reactants or assistants or give in at least one reaction step only relatively low conversions.

SUMMARY OF THE INVENTION

The invention is directed to a process of preparing tryptophane hydantoin by (a) reacting a compound of the general formula

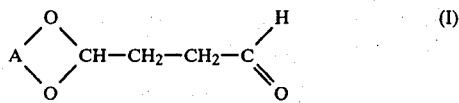

where A is an alkylene group having 2 or 3 carbon atoms or such an alkylene group substituted by 1 to 2 methyl groups in aqueous or aqueous alcoholic solution with hydrogen cyanide or a cyanide ion supplying compound, ammonia or an ammonium ion supplying compound and carbon dioxide or a carbonate ion supplying compound and (b) reacting the reaction mixture obtained with phenylhydrazine at a pH between 0.1 and 4.

The two reaction steps (a) and (b) of the process of the invention proceed with high conversions. Since the compounds employed of general formula (I) also are easily obtainable in high yields by hydroformylation of the corresponding 2-vinyl-1,3-dioxolane or 2-vinyl-1,3-dioxane and the latter are easily obtainable in high yields by acetalization of acrolein with the corresponding 1,2- or 1,3-glycols the process of the invention opens up a new inexpensive way to tryptophane-hydantoin starting from acrolein.

Examples of compounds of general formula (I) which can be employed are 2-(2'-formylethyl)-1,3-dioxolane, 2-(2'-formylethyl)-4-methyl-1,3-dioxolane, 2-(2'-formylethyl)-4,5-dimethyl-1,3-dioxolane, 2-(2'-formylethyl)-1,3-dioxane, 2-(2'-formylethyl)-4-methyl-1,3-dioxane and 2-(2'-formylethyl)-5,5-dimethyl-1,3-dioxane.

The compounds of general formula (I) are reacted in a first reaction step with hydrogen cyanide or a cyanide ion supplying compound such as sodium cyanide or potassium cyanide, with ammonia or an ammonium ion supplying compound such as ammonium hydroxide or ammonium chloride and with carbon dioxide or a carbonate ion supplying compound such as sodium or potassium bicarbonate, sodium or potassium carbonate or sodium or potassium carbamate in a manner known of itself for the formation of hydantoins from aldehydes. There can also be employed compounds which simultaneously supply cyanide and ammonium ions such as ammonium cyanide, or which simultaneously supply ammonium and carbonate ions such as ammonium carbonate or ammonium carbamate.

The reaction in the first step takes place in water or a mixture of water and methanol or ethanol. The ratio of water to alcohol is not critical. The reaction can be carried out within a wide temperature range. A temperature between 30° and 90° C. is preferred because in this range there is obtained a satisfactory speed of reaction and the superatmospheric pressure required if necessary forms no industrial obstacle.

The amounts of the individual reactants can be varied within wide limits. Preferably per mole of compound of general formula (I) there are employed 1 to 1.5 moles of hydrogen cyanide or a cyanide ion supplying compound, 2 to 15 moles of ammonia or an ammonium ion supplying compound and 1 to 2 moles of carbon dioxide or a carbonate ion supplying compound. The compounds of general formula (I) can be reacted simultaneously with all three other reactants. However, it is also likewise possible to first react them with the cyanide component and subsequently with the two other components simultaneously, or first to react them only with the cyanide component, then react only with the ammonium component and then react with the carbon dioxide or carbonate component. It is especially advantageous if the compounds of general formula (I) are dissolved in methanol or ethanol and this solution is fed in slowly to an aqueous solution or suspension of the other reactants heated to the desired reaction temperature. To attain a high conversion there is recommended an adequate post reaction time of, for example, about 5 hours after the end of the dosing in.

Depending on the reaction conditions the reaction mixture after carrying out the first reaction step contains besides the expected hydantoin of the general formula

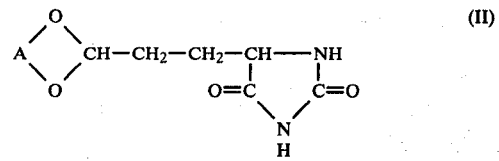

also a more or less large portion of the α-N-carbamoyl carboxylic acid amide of the general formula

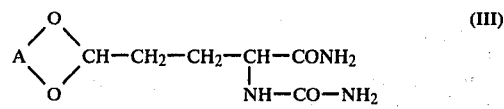

whereby in formulae (II) and (III) A is defined as stated above.

However, it is not necessary to separate the two reaction products since they both are changed in the subsequent reaction step (b) to tryptophane hydantoin. However, it can be suitable, before carrying out the second reaction step to boil off the ammonium salts contained in the crude reaction mixture of the first reaction step, to distill off the alcohol contained in a given case and to concentrate the reaction mixture under reduced pressure.

In reaction step (b) the mixture of compounds of general formulae (II) and (III) obtained in step (a) is reacted at a pH between 0.1 and 4 with phenyl hydrazine directly to the desired tryptophane hydantoin. The required pH between 0.1 and 4, preferably between 1 and 3 can be established by an inorganic acid, such as sulfuric acid or phosphoric acid, by an organic acid such as oxalic acid, formic acid, acetic acid, benzenesulfonic acid or p-toluenesulfonic acid or a strong acid ion exchanger, e.g. a sulfonated sytrene-divinyl benzene resin. It is preferred to use hydrochloric acid. Since there is set free in the formation of the desired tryptophane-hydantoin from the compounds of general formula (II) one molecule of ammonia and from the compounds of general formula (III) two molecules of ammonia, it is necessary in certain cases to adjust the pH during reaction step (b) by addition of acid. Likewise in the second reaction step the temperature can be varied within wide limits. Temperatures between 25° and 150° C., preferably between 70° and 120° C., are suitable.

The phenyl hydrazine can be employed in excess. However, on economical grounds it is more advantageous to use the amount which is equivalent to the compound of general formula (I) employed in reaction step (a).

The phenyl hydrazine can be mixed with the mixture obtained from reaction step (a) and the necessary amount of acid and be heated to the desired reaction temperature. However, it is likewise also possible to have present an acidic solution of phenyl hydrazine, to heat it and to slowly feed in the mixture obtained from reaction step (a). In both cases a reaction time in all of about 3 to 4 hours is generally sufficient. After the end of the reaction the solution of tryptophane-hydantoin can be concentrated and the residue recrystallized. However, the solution of tryptophane-hydantoin can also be brought to crystallization by cooling. The precipitate then is separated. The purity of the thus obtained product normally is over 95%. By recrystallization there is obtained pure tryptophane-hydantoin having a melting point of 213° to 216° C.

Unless otherwise stated all parts and percentages are by weight.

The process can comprise, consists essentially of or consist of the stated steps with the recited materials.

The invention is made more clear by the following examples.

EXAMPLE 1

32.5 grams of 2-(2'-formylethyl)-1,3-dioxolane were dropped into a suspension of 96 grams ammonium carbonate, 10.2 grams of hydrocyanic acid and 220 ml of aqueous ammonia (25%) at 35° C. in the course of one hour and the mixture was subsequently stirred for five hours at 40° C. Subsequently by increasing the temperature (up to 100° C. head temperature) the salts were boiled out. The remaining aqueous solution was adjusted to pH 1 with concentrated hydrochloric acid and in the course of one hour at 90° C. slowly dropped into a stirred solution of 27 grams of phenyl hydrazine in 600 ml of 0.1 N HCl. The reaction mixture was subsequently held for a further two hours at the temperature of 90° C. After slow cooling to 10° C. the precipitate formed was filtered off and dried at reduced pressure. The yield of tryptophane-hydantoin was 45.8 grams (80% of theory).

Elemental analysis: $C_{12}H_{11}N_3O_2$. Calculated: C, 62.9%; H, 4.8%; N, 18.3%. Found: C, 61.6%; H, 4.9%; N, 18.2%.

EXAMPLE 2

35.5 grams of 2-(2'-formylethyl)-4-methyl-1,3-dioxolane were dropped into a suspension of 96 grams of ammonium carbonate, 10.2 grams of hydrocyanic acid and 100 ml of aqueous ammonia (25%) at 40° C. in the course of one hour and the mixture was further stirred for four hours at 60° C. After the boiling out of the salts at 100° C. the remaining aqueous solution was adjusted to pH 1.5 with concentrated hydrochloric acid and added at 95° C. to a stirred solution of 36.5 grams of phenyl hydrazine hydrochloride in 750 ml of 0.1 N HCl. Subsequently stirring was continued for two hours at 95° C. After cooling to 10° C. the precipitate formed was filtered off and dried at reduced pressure. The yield of tryptophane-hydantoin was 42.4 grams (74% of theory).

EXAMPLE 3

In an analogous manner to Example 1 15.8 grams of 2-(2'-formylethyl)-4,5-dimethyl-1,3-dioxolane were reacted with 35 grams of ammonium carbonate, 4.1 grams of hydrocyanic acid and 100 ml of aqueous ammonia (25%). The thus obtained aqueous solution was stirred with 10.8 grams of phenyl hydrazine in 240 ml of 0.1 N HCl at 90° C. The yield of tryptophane-hydantoin was 16.2 grams (71% of theory).

EXAMPLE 4

A solution of 41.4 grams of 2-(2'-formylethyl)-1,3-dioxane in 100 ml of methanol was dropped into a suspension of 83 grams of ammonium carbonate, 11.7 grams of hydrocyanic acid and 250 ml of aqueous ammonia (25% aqueous solution) at 50° C. in the course of one hour and the mixture was stirred for a further three hours at 50° C. Subsequently the methanol was distilled off up to a head temperature of 100° C. and the salts boiled off. The remaining aqueous solution was adjusted to pH 1.2 with concentrated hydrochloric acid and at 90° C. in the course of 1.5 hours dropped into a stirred solution of 31 grams of phenyl hydrazine in 750 ml of 0.1 N HCl. Subsequently the reaction mixture was held for a further hour at the temperature of 90° C. After cooling to 10° C. the precipitate formed was filtered off and dried at reduced pressure. The yield of tryptophane-hydantoin was 48.8 grams (74% of theory).

EXAMPLE 5

In a manner analogous to Example 4, 45.5 grams of 2-(2'-formylethyl)-4-methyl-1,3-dioxane were converted into tryptophane-hydantoin. The yield was 52.7 grams (80% of theory).

EXAMPLE 6

A solution of 43 grams of 2-(2'-formylethyl)-5,5-dimethyl-1,3-dioxane in 50 ml of methanol was dropped into a suspension of 72 grams of ammonium carbonate, 10.2 grams of hydrocyanic acid and 175 ml of aqueous ammonia (25%) at 35° C. in the course of one hour and the mixture was subsequently stirred for a further four hours at 50° C. Subsequently the methanol was distilled off and the ammonium salts boiled off at 100° C. The remaining aqueous solution was cooled down to 80° C., adjusted with concentrated hydrochloric acid to pH 1.5 and at the given temperature in the course of two hours dropped into a stirred solution of 27 grams of phenyl hydrazine in 600 ml of 0.1 N HCl heated to 90° C. Subsequently the mixture was stirred for a further hour at 95° C. and slowly cooled to 10° C. The precipitate formed was filtered off and dried at reduced pressure. The yield of tryptophane-hydantoin was 45.3 grams (79% of theory).

EXAMPLE 7

A solution of 16.3 grams of 2-(2'-formylethyl)-1,3-dioxolane in 100 ml of ethanol was dropped into a suspension of 48 grams of ammonium carbonate, 5.1 grams of hydrocyanic acid and 120 ml of aqueous ammonia (25%) at 35° C. and the mixture was stirred for a further five hours at 60° C. The thus obtained solution was adjusted to pH 1 with concentrated hydrochloric acid and it was added at room temperature to a solution of 13.5 grams of phenyl hydrazine in 300 ml of 0.1 N HCl. The reaction mixture was heated at 90° C. for two hours, cooled and concentrated at reduced pressure. The residue was recrystallized from a mixture of water-/ethanol (50:50 by volume). The yield of tryptophane-hydantoin was 19.7 grams (68.5% of theory).

What is claimed is:

1. A process of preparing tryptophane hydantoin comprising (a) reacting a compound of formula

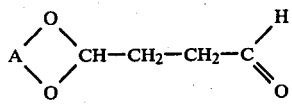

(I)

where A is an alkylene group having 2 or 3 carbon atoms or such an alkylene group substituted by 1 to 2 methyl groups in aqueous or aqueous-alcoholic solution with hydrogen cyanide or a cyanide ion supplying compound, ammonia or an ammonium ion supplying compound and carbon dioxide or a carbonate ion supplying compound and (b) reacting the reaction mixture obtained with phenyl hydrazine at a pH between 0.1 and 4.

2. A process according to claim 1 wherein in reaction step (a) the hydrogen cyanide or cyanide ion supplying compound is employed in an amount between 1 and 1.5 moles, the ammonia or ammonium ion supplying compound is employed in an amount between 2 and 15 moles and the carbon dioxide or carbonate ion supplying compound is employed in an amount between 1 and 2 moles, in each case per mole of the compound of formula (I).

3. A process according to claim 2 wherein reaction step (a) is carried out at a temperature between 30° and 90° C.

4. A process according to claim 1 wherein reaction step (a) is carried out at a temperature between 30° and 90° C.

5. A process according to claim 4 wherein reaction step (b) is carried out at a temperature between 25° and 150° C.

6. A process according to claim 3 wherein reaction step (b) is carried out at a temperature between 25° and 150° C.

7. A process according to claim 2 wherein reaction step (b) is carried out at a temperature between 25° and 150° C.

8. A process according to claim 1 wherein reaction step (b) is carried out at a temperature between 25° and 150° C.

9. A process according to claim 1 wherein the compound of formula (I) is 2(2'-formylethyl)-1,3-dioxolane, 2-(2'-formylethyl)-4-methyl-1,3-dioxolane, 2,(2'-formylethyl)-4,5-dimethyl-1,3-dioxolane, 2-(2'-formylethyl)-1,3-dioxane, 2-(2'-formylethyl)-4-methyl-1,3-dioxane or 2-(2'-formylethyl)-5,5-dimethyl-1,3-dioxane, the hydrogen cyanide or cyanide ion supplying compound is hydrocyanic acid, the ammonia or ammonium ion supplying compound is ammonia itself or ammonium carbonate and the carbon dioxide or carbonate ion supplying compound is carbon dioxide itself or ammonium carbonate.

10. A process according to claim 2 wherein the compound of formula (I) is 2-(2'-formylethyl)-1,3-dioxolane, 2-(2'-formylethyl)-4-methyl-1,3-dioxolane, 2,(2'-formylethyl)-4,5-dimethyl-1,3-dioxolane, 2-(2'-formylethyl)-1,3-dioxane, 2-(2'-formylethyl)-4-methyl-1,3-dioxane or 2-(2'-formylethyl)-5,5-dimethyl-1,3-dioxane, the hydrogen cyanide or cyanide ion supplying compound is hydrocyanic acid, the ammonia or ammonium ion supplying compound is ammonia itself or ammonium carbonate and the carbon dioxide or carbonate ion supplying compound is carbon dioxide itself or ammonium carbonate.

* * * * *